(12) United States Patent
Bai et al.

(10) Patent No.: US 9,636,411 B2
(45) Date of Patent: May 2, 2017

(54) LARGE SCALE PROCESS FOR PREPARING POLY (GLUTAMYL-GLUTAMATE) CONJUGATES

(71) Applicant: NITTO DENKO CORPORATION, Osaka (JP)

(72) Inventors: Hao Bai, San Diego, CA (US); Kwok Yin Tsang, Irvine, CA (US); Yi Jin, Carlsbad, CA (US); Lei Yu, Carlsbad, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 14/786,841

(22) PCT Filed: Apr. 26, 2013

(86) PCT No.: PCT/US2013/038492
§ 371 (c)(1),
(2) Date: Oct. 23, 2015

(87) PCT Pub. No.: WO2014/175898
PCT Pub. Date: Oct. 30, 2014

(65) Prior Publication Data
US 2016/0074524 A1    Mar. 17, 2016

(51) Int. Cl.
| C08G 63/02 | (2006.01) |
| A61K 47/48 | (2006.01) |
| C08G 69/10 | (2006.01) |
| C08G 73/02 | (2006.01) |
| C08G 64/00 | (2006.01) |

(52) U.S. Cl.
CPC .. *A61K 47/48207* (2013.01); *A61K 47/48315* (2013.01); *C08G 69/10* (2013.01); *C08G 73/028* (2013.01)

(58) Field of Classification Search
CPC ................ A61K 47/48207; C08G 73/028
USPC ............ 525/417; 528/313, 315, 324, 328
See application file for complete search history.

(56) References Cited

U.S. PATENT DOCUMENTS

| 8,329,853 B2 * | 12/2012 | McKennon ......... C07K 14/001 528/328 |
| 2002/0128177 A1 | 9/2002 | Kirk et al. |
| 2007/0128118 A1 | 6/2007 | Yu et al. |
| 2008/0181852 A1 | 7/2008 | Yu et al. |
| 2008/0279778 A1 | 11/2008 | Van et al. |
| 2013/0178415 A1 * | 7/2013 | Soula ..................... A61K 47/34 514/6.5 |

FOREIGN PATENT DOCUMENTS

| JP | 2009/518511 | 5/2009 |
| JP | 2010/516783 | 5/2010 |
| JP | 2011/513412 | 4/2011 |
| WO | WO 2007/067417 | 6/2007 |
| WO | WO 2008/094834 | 8/2008 |
| WO | WO 2009/111271 | 9/2009 |
| WO | WO 2014/175899 | 10/2014 |

OTHER PUBLICATIONS

Giovannucci Edward et al., Diabetes and Cancer, ADA Consensus Report, Diabetes Care Jul. 2010; 33(7): 1674-1685.*
International Written Opinion and Search Report mailed on Jul. 29, 2013 in International Application No. PCT/US2013/038492, filed on Apr. 26, 2013.
IUPAC-IUP Commission of Biochemical Nomenclature Biochem. vol. 11: 942-944 1972.
Extended European Search Report for European Application 13882675.5 dated Dec. 9, 2016.
Office Action in Japanese Patent Application 2016-510657 dated Jan. 4, 2017, with English Translation.
Sun et al "Challenges in design of translational nanocarriers" Journal of Controlled Release vol. 164 2012 156-169.
Van et al "Synthesis, characterization, and biological evaluation of poly(L-gamma-glutamyl-glutamine)-paclitaxel nanoconjugate" International Journal of Nanomedicine May 2010 825-837.

* cited by examiner

*Primary Examiner* — Terressa Boykin
(74) *Attorney, Agent, or Firm* — Knobbe Martens Olson & Bear LLP

(57) ABSTRACT

Described herein are processes of making biocompatible water-soluble polymers conjugates. In particular, large scale processes of making poly(L-γ-glutamyl-glutamate) conjugates that can be useful for a variety of drug delivery applications are described herein.

41 Claims, No Drawings

LARGE SCALE PROCESS FOR PREPARING POLY (GLUTAMYL-GLUTAMATE) CONJUGATES

BACKGROUND

Field

This application relates generally to processes of making biocompatible water-soluble polymers conjugates. In particular, this application relates to large scale processes of making poly(L-γ-glutamyl-glutamate) conjugates that can be useful for a variety of drug delivery applications.

Description

Amino acid-based polymers have been considered as a potential source of new biomaterials. Poly-amino acids having good biocompatibility have been investigated to deliver low molecular-weight compounds. A relatively small number of polyglutamic acids and copolymers have been identified as candidate materials for drug delivery.

SUMMARY

Some embodiments described herein generally relate to a process of manufacture for preparing batches of a poly(L-γ-glutamyl-glutamate)-anticancer drug conjugate that can include polymerizing a compound of Formula (A) to form a polymer having recurring units of Formula (I), wherein $R^1$ can be selected from $C_{1-6}$ alkyl, an optionally substituted phenyl and an optionally substituted benzyl;

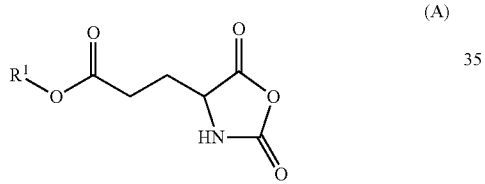

(A)

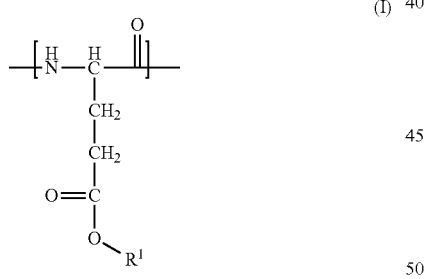

(I)

forming the alkali metal salt of the recurring unit of Formula (I); reacting the alkali metal salt of the recurring unit of Formula (I) with a compound of Formula (B) to form a polymer having recurring units of Formula (II), wherein each $R^2$ can be independently selected from $C_{1-6}$ alkyl, an optionally substituted phenyl and an optionally substituted benzyl;

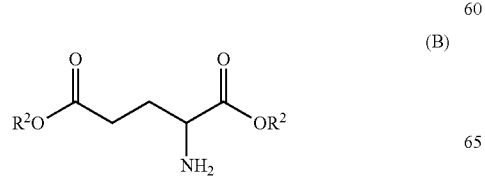

(B)

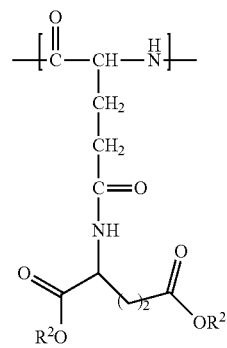

(II)

removing the $R^2$ groups from the recurring units of Formula (II) to form a polymer having recurring units Formula (III); and

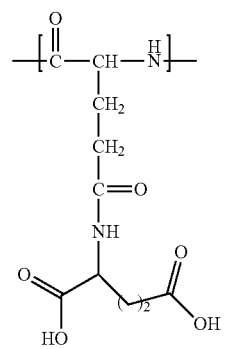

(III)

reacting an anticancer drug with a portion of the recurring units of Formula (III) to form the poly(L-γ-glutamyl-glutamate)-anticancer drug conjugate, wherein the poly(L-γ-glutamyl-glutamate)-anticancer drug conjugate can include recurring units of Formula (IV) and recurring units of Formula (V):

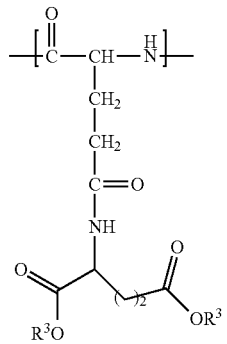

(IV)

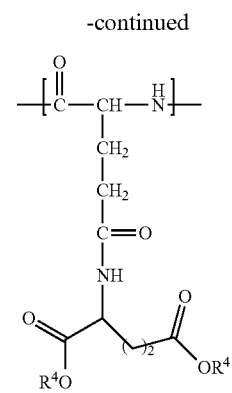

(V)

wherein: each R³ can be independently hydrogen or an alkali metal; and each R⁴ can be independently hydrogen, an alkali metal or the anticancer drug, provided that at least one R⁴ is the anticancer drug; wherein at least 3 batches of poly(L-γ-glutamyl-glutamate)-anticancer drug conjugate are prepared; wherein each batch can provide an amount of the poly(L-γ-glutamyl-glutamate)-anticancer drug conjugate greater than or equal to about 300 grams; and wherein each batch of the poly(L-γ-glutamyl-glutamate)-anticancer drug conjugate has one or more characteristics selected from a weight average molecular weight within a certain number of kDa from each other batch, a similar polydispersity and low endotoxin content.

DETAILED DESCRIPTION

Unless defined otherwise, all technical and scientific terms used herein have the same meaning as is commonly understood by one of ordinary skill in the art. All patents, applications, published applications and other publications referenced herein are incorporated by reference in their entirety, unless stated otherwise. In the event that there are a plurality of definitions for a term, those in this section prevail unless stated otherwise.

The term "polymer conjugate" is used herein in its ordinary sense and thus includes polymers that are attached to one or more types of biologically active agents or drugs, such as paclitaxel. For example, PGGA-PTX as described herein is a polymer conjugate in which poly-(γ-L-glutamyl-glutamate) (PGGA) is attached to paclitaxel (PTX). The polymer (e.g., PGGA) may be attached directly to the biologically active agent or drug (e.g., PTX), or may be attached through a linker group. The linker group may be a relatively small chemical moiety such as an ester or amide bond, or may be a larger chemical moiety, e.g., an alkyl ester linkage or an alkylene oxide linkage.

As used herein, "$C_m$ to $C_n$" in which "m" and "n" are integers that refer to the number of carbon atoms in a group or the number of carbons in a ring(s). That is, the group or ring can contain from "m" to "n", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$—, $CH_3CH(CH_3)CH_2$— and $(CH_3)_3C$—. If no "m" and "n" are designated, the broadest range described in the definitions provided herein is to be assumed.

As used herein, "alkyl" refers to a straight or branched fully saturated (no double or triple bonds) hydrocarbon group, for example, a group having the general formula —$C_nH_{2n+1}$. The alkyl group may have 1 to 50 carbon atoms (whenever it appears herein, a numerical range such as "1 to 50" refers to each integer in the given range; e.g., "1 to 50 carbon atoms" means that the alkyl group may consist of 1 carbon atom, 2 carbon atoms, 3 carbon atoms, etc., up to and including 50 carbon atoms, although the present definition also covers the occurrence of the term "alkyl" where no numerical range is designated). The alkyl group may also be a medium size alkyl having 1 to 30 carbon atoms. The alkyl group could also be a lower alkyl having 1 to 5 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl and the like.

The alkyl group may be substituted or unsubstituted. When substituted, the substituent group(s) is(are) one or more group(s) individually and independently selected from alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, ester, mercapto, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof.

As used herein, "aryl" refers to a hydrocarbon monocyclic or multicyclic aromatic ring system that has a fully delocalized pi-electron system throughout all the rings. Examples of aryl groups include, but are not limited to, benzene (phenyl), naphthalene and azulene. The ring(s) of the aryl group may have 5 to 50 carbon atoms. The aryl group may be substituted or unsubstituted.

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl, and naphthylalkyl.

Unless otherwise indicated, when a substituent is "optionally substituted," or "substituted" it is meant that the substituent is a group that may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. The protecting groups that may form the protective derivatives of the above substituents are known to those of skill in the art and may be found in references such as Greene and Wuts, Protective Groups in Organic Synthesis, 3$^{rd}$ Ed., John Wiley & Sons, New York, N.Y., 1999, which is hereby incorporated by reference in its entirety.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. In addition it is understood that, in any compound having one or more double bond(s) generating geometrical isomers that can be defined as E or Z each double bond may independently be E or Z or a mixture thereof. Likewise, all tautomeric forms are also intended to be included.

As used herein, the abbreviations for any protective groups, amino acids and other compounds are, unless indicated otherwise, in accord with their common usage, recognized abbreviations, or the IUPAC-IUP Commission on Biochemical Nomenclature (See, Biochem. 11:942-944 (1972)).

Some embodiments described herein generally relate to a process of manufacture for preparing multiple batches of a poly(L-γ-glutamyl-glutamate)-anticancer drug conjugate that can include recurring units of Formula (IV) and recurring units of Formula (V), wherein each batch can provide the poly(L-γ-glutamyl-glutamate)-anticancer drug conjugate in an amount greater than or equal to about 300 grams, and wherein each batch of the poly(L-γ-glutamyl-glutamate)-anticancer drug conjugate has one or more characteristics selected from a weight average molecular weight within a certain number of kDa from each other batch, a similar polydispersity and low endotoxin content.

The processes described herein can be used to prepare a polymer conjugate described herein (for example, a polymer conjugate that includes recurring units of Formula (IV) and recurring units of Formula (V)) on a large scale. In some embodiments, a process described herein can be used to prepare a single batch of the polymer conjugate in an amount greater than about 300 grams. In some embodiments, a process described herein can be used to prepare a single batch of the polymer conjugate in an amount greater than about 0.8 kilograms. In some embodiments, a process described herein can be used to prepare a single batch of the polymer conjugate in an amount greater than about 1.0 kilograms. In some embodiments, a process described herein can be used to prepare a single batch of the polymer conjugate in an amount in the range of about 300 grams to about 1.5 kilograms. In other embodiments, a process described herein can be used to prepare a single batch of the polymer conjugate in an amount in the range of about 0.5 kg to about 5 kilograms. In still other embodiments, a process described herein can be used to prepare a single batch of the polymer conjugate in an amount in the range of about 0.8 kilograms to about 3 kilograms.

The processes described herein can provide highly consistent batches of the polymer conjugate (for example, a polymer conjugate that includes recurring units of Formula (IV) and recurring units of Formula (V)). Some embodiments described herein are generally related to a highly reproducible process of manufacture that can include preparing batches of a polymer conjugate described herein (for example, a polymer conjugate that includes recurring units of Formula (IV) and recurring units of Formula (V)), wherein each batch of polymer conjugate has a weight average molecular weight within a certain number of kDa from each other batch, a similar polydispersity and/or low endotoxin content. For example, 5 batches of a polymer conjugate are prepared using a process described herein, wherein each of the 5 batches has a weight average molecular weight of 70 kDa, 76 kDa, 72 kDa, 77 kDa and 78 kDa, respectively, and weight average molecular weights within ±8 kDa of each other. In some embodiments, at least 3 batches of the polymer conjugate can be prepared. In some embodiments, at least 10 batches of the polymer conjugate can be prepared. In some embodiments, at least 25 batches of the polymer conjugate can be prepared. In some embodiments, batches in the range of 3 to 100 of the polymer conjugate can be prepared.

In some embodiments, the batches of polymer conjugate can have weight average molecular weights within ±10 kDa of each other. In some embodiments, the batches of polymer conjugate can have weight average molecular weights within ±5 kDa of each other. In some embodiments, the batches of polymer conjugate can have weight average molecular weights within ±2 kDa of each other. In some embodiments, the batches of polymer conjugate can have weight average molecular weights within ±1 kDa of each other.

Various molecular weights of the polymer conjugate can be obtained from a process described herein. In some embodiments, each batch of a poly(L-γ-glutamyl-glutamate)-anticancer drug conjugate obtained from a process described herein can have a weight average molecular weight in the range of about 10 kDa to about 150 kDa. In other embodiments, each batch of a poly(L-γ-glutamyl-glutamate)-anticancer drug conjugate obtained from a process described herein can have a weight average molecular weight in the range of about 30 kDa to about 120 kDa. In still other embodiments, each batch of a poly(L-γ-glutamyl-glutamate)-anticancer drug conjugate obtained from a process described herein can have a weight average molecular weight in the range of about 60 kDa to about 100 kDa. In yet still other embodiments each batch of a poly(L-γ-glutamyl-glutamate)-anticancer drug conjugate obtained from a process described herein can have a weight average molecular weight equal to or less than about 100 kDa. In some embodiments, each batch of a poly(L-γ-glutamyl-glutamate)-anticancer drug conjugate obtained from a process described herein can have a weight average molecular weight equal to or greater than about 60 kDa.

Processes of preparing a polymer conjugate described herein can provide a polymer conjugate (for example, a polymer conjugate that includes recurring units of Formulae (IV) and (V)) with a narrow polydispersity index. For example, in some embodiments, the polydispersity index of a polymer conjugate (for example, poly(L-γ-glutamyl-glutamate)-anticancer drug conjugate) of a batch obtained from a process described herein can be less than 2.0. In some embodiments, each batch of a polymer conjugate obtained from a process described herein can be a polydispersity index less than 1.7. In some embodiments, each batch of a polymer conjugate obtained from a process described herein can be a polydispersity index less than 1.5. In other embodiments, each batch of a polymer conjugate obtained from a process described herein can be a polydispersity index in the range of about 1.0 to about 2.0. In some embodiments, each batch of a polymer conjugate obtained from a process described herein can be a polydispersity index in the range of 1.0 to 1.5. In some embodiments, the batches of polymer conjugate can have polydispersities within ±0.5 of each other. In other embodiments, the batches of polymer conjugate can have polydispersities within ±0.1 of each other. In still other embodiments, the batches of polymer conjugate can have polydispersities within ±0.05 of each other.

Further, processes of preparing a polymer conjugate described herein (for example, poly(L-γ-glutamyl-glutamate)-anticancer drug conjugate) can provide a polymer conjugate with a low endotoxin content. Endotoxins, also called lipopolysaccharides (LPS), are contaminants found in commercially available proteins or biologically active substances. The presence of small amounts of endotoxins in recombinant protein preparations can cause side effects in a host organism, such as endotoxin shock, tissue injury, and even death. Due to these side effects, reducing the amount of endotoxins present in biological and pharmaceutical products is desirable. In some embodiments, a process described herein can provide batches of a polymer conjugate (for example, a poly(L-γ-glutamyl-glutamate)-anticancer drug conjugate) with an endotoxin content of less than 0.25 EU/mg. In some embodiments, a process described herein can provide batches of a polymer conjugate with an endotoxin content of less than 0.20 EU/mg. In some embodiments, a process described herein can provide batches of a polymer conjugate with an endotoxin content of less than 0.15 EU/mg. In some embodiments, a process described herein can provide batches of a polymer conjugate (for example, a poly(L-γ-glutamyl-glutamate)-anticancer drug conjugate) with an endotoxin content of less than 0.1 EU/mg. Methods for measuring endotoxin content are known to those skilled in the art. One example is the limulus amebocyte lysate (LAL) assay. In some embodiments, including those of this paragraph, the amount of endotoxins present in a polymer conjugate described herein (for example, a poly(L-γ-glutamyl-glutamate)-anticancer drug conjugate) can be measured using the LAL assay.

The percentage of recurring units of Formula (IV) and recurring units of Formula (V) in the polymer conjugate, based on the total number of recurring units, may vary over a wide range. In some embodiments, the percentage of recurring units Formula (IV) and recurring units of Formula (V) can be in the range of about 80 mole % to about 99 mole % based on the total moles of recurring units in the polymer conjugate. In other embodiments, the percentage of recurring units Formula (IV) and recurring units of Formula (V) can be in the range of about 90 mole % to about 99 mole % based on the total moles of recurring units in the polymer conjugate. In still other embodiments, the percentage of recurring units Formula (IV) and recurring units of Formula (V) can be in the range of about 95 mole % to about 99 mole % based on the total moles of recurring units in the polymer conjugate. In yet still other embodiments, the percentage of recurring units Formula (IV) and recurring units of Formula (V) can be greater than about 99 mole % based on the total moles of recurring units in the polymer conjugate. In some embodiments, the poly(L-γ-glutamyl-glutamate)-anticancer drug conjugate can consist of, or consist essentially of recurring units of Formula (IV) and recurring units of Formula (V).

In some embodiments, the polymer conjugates described herein can include an alkali metal. Examples of alkali metals include lithium (Li), sodium (Na), potassium (K), rubidium (Rb), and cesium (Cs). In some embodiments, the alkali metal can be sodium.

In some embodiments, the polymer conjugate can be in the acid form. In other embodiments, the polymer conjugate can be in the alkali metal salt form. In some embodiments, at least 90% of the $R^3$ groups can be hydrogen and at least 90% of the $R^4$ groups that are not an anticancer drug can be hydrogen. In some embodiments, at least 95% of the $R^3$ groups can be hydrogen and at least 95% of the $R^4$ groups that are not an anticancer drug can be hydrogen. In some embodiments, greater than 98% of the $R^3$ groups can be hydrogen and greater than 98% of the $R^4$ groups that are not an anticancer drug can be hydrogen. In other embodiments, at least 90% of the $R^3$ groups can be an alkali metal and at least 90% of the $R^4$ groups that are not an anticancer drug can be an alkali metal. In other embodiments, at least 95% of the $R^3$ groups can be an alkali metal and at least 95% of the $R^4$ groups that are not an anticancer drug can be an alkali metal. In other embodiments, greater than 98% of the $R^3$ groups can be an alkali metal and greater than 98% of the $R^4$ groups that are not an anticancer drug can be an alkali metal.

A variety of anticancer drugs can be attached to the polymer to form the polymer conjugate. In some embodiments, the anticancer drug can be selected from a taxane, a camptotheca, and an anthracycline. In some embodiments, the camptotheca can be camptothecin. In some embodiments, the anthracycline can be doxorubicin. Examples of taxanes include, but are not limited to, paclitaxel and docetaxel. In some embodiments, the taxane can be paclitaxel. In some embodiments, when the anticancer drug is paclitaxel, the paclitaxel can be attached to a recurring unit of Formula (V) at the oxygen atom attached to the C2'-carbon of the paclitaxel. In other embodiments, the paclitaxel can be attached to a recurring unit of Formula (V) at the oxygen atom attached to the C7-carbon of the paclitaxel.

The amount of the anticancer drug present in the polymer conjugate can vary over a wide range. In some embodiments, the polymer conjugate can include a total amount of the anticancer drug in the range of about 5% to about 50% (weight/weight) of the anticancer drug based on the mass ratio of the anticancer drug to the poly(L-γ-glutamyl-glutamate)-anticancer drug conjugate. In other embodiments, the polymer conjugate can include a total amount of the anticancer drug in the range of about 10% to about 40% (weight/weight) of the anticancer drug based on the mass ratio of the anticancer drug to the poly(L-γ-glutamyl-glutamate)-anticancer drug conjugate. In still other embodiments, the polymer conjugate can include a total amount of the anticancer drug in the range of about 20% to about 40% (weight/weight) of the anticancer drug based on the mass ratio of the anticancer drug to the poly(L-γ-glutamyl-glutamate)-anticancer drug conjugate. In yet still other embodiments, the polymer conjugate can include a total amount of the anticancer drug in the range of about 30% to about 40% (weight/weight) of the anticancer drug based on the mass ratio of the anticancer drug to the poly(L-γ-glutamyl-glutamate)-anticancer drug conjugate.

The total number of recurring units of Formula (IV) and (V) present in the poly(L-γ-glutamyl-glutamate)-anticancer drug conjugate described herein can vary. The total number of recurring units of the Formulae (IV) and (V) in the polymer conjugate can vary over a broad range, such as in the range of from about 40 to about 1,000, or in the range of from about 50 to about 500.

In some embodiments, the polymer conjugates described herein can include other recurring units that are not of the Formulae (IV) and (V), such that the polymer conjugate is a copolymer conjugate. A broad variety of other recurring units may be included in a polymer conjugate described herein. An example of a suitable recurring unit is the following:

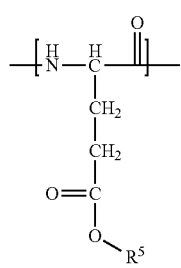

(VI)

wherein $R^5$ can be hydrogen or an alkali metal (for example, an alkali metal described herein).

As described herein, a poly(L-γ-glutamyl-glutamate)-anticancer drug conjugate that can be prepared from a compound of Formula (A). A compound of Formula (A) can be prepared using various methods, including those known to those skilled in the art. Those skilled in the art understand a compound of Formula (A) is an α-amino acid-N-carboxyanhydride (NCA)-ester. In some embodiments, a compound of Formula (A) can be prepared from a compound of Formula (1):

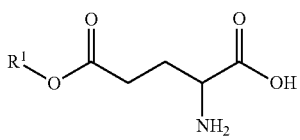

(1)

wherein $R^1$ can be selected from $C_{1-6}$ alkyl, an optionally substituted phenyl and an optionally substituted benzyl. Examples of suitable reagents for preparing a compound of Formula (A) from a compound of Formula (1) include triphosgene and phosgene. The reaction can be conducted in one or more suitable solvents, for example water-miscible solvent(s). In some embodiments, the solvent can be tetrahydrofuran (THF).

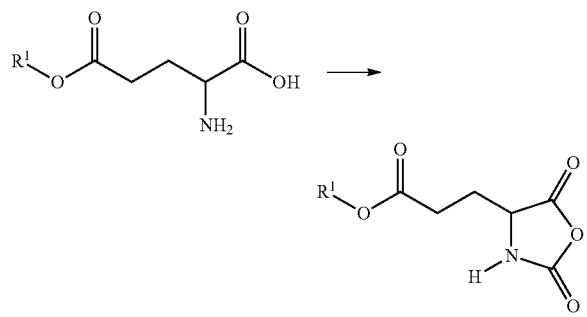

A compound of Formula (A) can be polymerized to form a polymer having recurring units of Formula (I). Polymerization of a compound of Formula (A) can be initiated by a nucleophile, base and/or a transition metal complex. In some embodiments, the initiator can be an amine (such as a primary amine, secondary amine and/or tertiary amine). In other embodiments, the initiator can be an alkoxide (for example, NaOMe). The polymer can be formed via a nucleophilic ring-opening chain growth process and/or by deprotecting the compound of Formula (A) to form a nucleophile that initiates the chain growth process. Polymerization of NCA has several obstacles including the presence of side reactions, such as chain termination and/or chain transfer. These side reactions can inhibit the ability to control the molecular weight of the resulting polymer and/or provide broad weight distributions. In addition, impurities in the NCA starting material can interfere with the polymerization by quenching the polymer chain. Examples of impurities include traces of acid, acid chlorides and isocyanates.

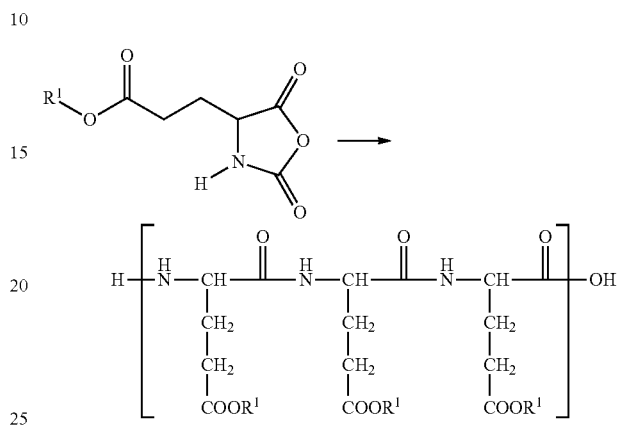

In some embodiments, $R^1$ of a compound of Formula (A) and/or recurring units of Formula (I) can be $C_{1-6}$ alkyl. In other embodiments, $R^1$ of a compound of Formula (A) and/or recurring units of Formula (I) can be an optionally substituted phenyl. In still other embodiments, $R^1$ of a compound of Formula (A) and/or recurring units of Formula (I) can be an optionally substituted benzyl.

The $R^1$ groups can be removed by a variety of methods. For example, $R^1$ can be cleaved using an acid solution. In some embodiments, the acid solution can include one or more acids. In some embodiments, the acid solution can include at least two acids. As an example, the acid solution can be a solution of hydrobromic acid and acetic acid. In other embodiments, the acid solution can include one acid. Suitable acids for removing the $R^1$ groups include, but are not limited to the following: hydrochloric acid, hydrobromic acid, nitric acid, nitrous acid, sulfuric acid, sulfonic acid, acetic acid, formic acid, trichloroacetic acid, dichloroacetic acid, chloroacetic acid, glyoxylic acid, oxalic acid, glycolic acid, phosphoric acid, phosphorous acid, malonic acid and trifluoroacetic acid.

The alkali metal salt of poly(glutamic) acid (PGA) can be formed using an alkali metal base. In some embodiments, the alkali metal salt of PGA that can be formed is poly (glutamate-sodium salt) (PGA-Na). Various alkali metal bases can be used. Examples of suitable alkali metal bases include an alkali metal bicarbonate, an alkali metal carbonate and an alkali metal hydroxide. In some embodiments, the alkali metal base can be sodium bicarbonate. In other embodiments, the alkali metal base can be sodium hydroxide.

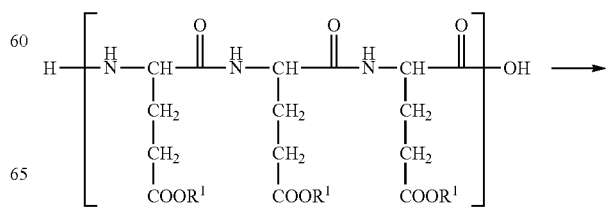

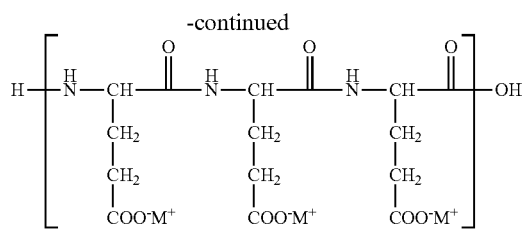

wherein M⁺ is an alkali metal

Formation of poly(glutamyl-glutamate) (PGGA) can be accomplished using various methods. In some embodiments, a compound of Formula (B) can be reacted with a polymer having recurring units of Formula (I) to form a polymer that can include recurring units of Formula (II), wherein each $R^2$ can be independently selected from $C_{1-6}$ alkyl, an optionally substituted phenyl and an optionally substituted benzyl. In some embodiments, $R^2$ can be a $C_{1-6}$ alkyl. For example, $R^2$ can be t-butyl. In other embodiments, $R^2$ can be an optionally substituted phenyl. In still other embodiments, $R^2$ can be an optionally substituted benzyl.

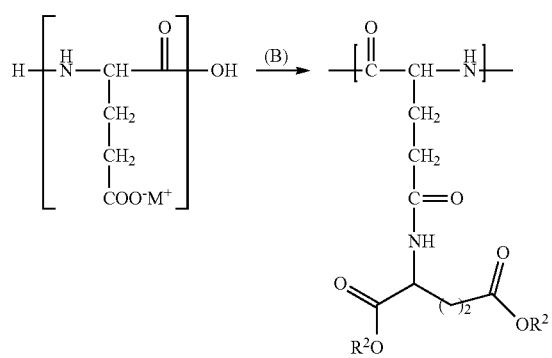

As discussed herein, a polymer conjugate can include other recurring units besides recurring units of Formulae (IV) and (V), for example, recurring units of Formula (VI). One method for forming a polymer that includes recurring units of the Formulae (IV), (V) and (VI) is by reacting the alkali metal salt of a polymer that includes recurring units of Formula (I) with less than 1.0 equivalents of a compound of Formula (B). For example, the alkali metal salt of a polymer that includes recurring units of the Formula (I) can be reacted with 0.85 equivalents of a compound of Formula (B).

In some embodiments, the reaction of the alkali metal salt of a polymer that can include recurring units of Formula (I) with a compound of Formula (B) can further include the use of a coupling agent. Examples of suitable coupling reagents include: 1-ethyl-3-(3-dimethylaminopropyl)-carbodiimide (EDC), 1,3-dicyclohexyl carbodiimide (DCC), 1,1'-carbonyl-diimidazole (CDI), N,N'-disuccinimidyl carbonate (DSC), N-[(dimethylamino)-1H-1,2,3-triazolo-[4,5-b]pyridine-1-yl-methylene]-N-methylmethanaminium hexafluorophosphate N-oxide (HATU), 2-[(1H-benzotriazol-1-yl)-1, 1,3,3-tetramethylaminium hexafluorophosphate (HBTU), 2-[(6-chloro-1H-benzotriazol-1-yl)-1,1,3,3-tetramethylaminium hexafluorophosphate (HCTU), benzotriazole-1-yl-oxy-tris-pyrrolidino-phosphonium hex afluorophosphate (PyBOP®)), bromo-tris-pyrrolidino-phosphonium hexafluorophosphate (PyBroP®), 2-[(1H-benzotriazol-1-yl)-1,1,3,3-tetramethylaminium tetrafluoroborate (TBTU), and benzotriazol-1-yl-oxy-tris-(dimethylamino)phosphonium hexafluorophosphate (BOP). The reaction can be conducted in a suitable solvent, such as N,N-dimethylformamide (DMF), dimethyl sulfoxide (DMSO), N-methyl-2-pyridone (NMP), and N,N-dimethylacetamide (DMA). In some embodiments, the solvent can be DMF.

A polymer having recurring units of Formula (III) can be obtained by removing the $R^2$ groups from the recurring units of Formula (II). A variety of methods and conditions can be used for removing the $R^2$ groups. For example, the $R^2$ groups can be removed by hydrolysis using an acid or a base. Suitable acids include, but are not limited to, hydrochloric acid, hydrobromic acid, nitric acid, nitrous acid, sulfuric acid, sulfonic acid, acetic acid, formic acid, trichloroacetic acid, dichloroacetic acid, chloroacetic acid, glyoxylic acid, oxalic acid, glycolic acid, phosphoric acid, phosphorous acid, malonic acid and trifluoroacetic acid. In some embodiments, $R^2$ groups can be removed using trifluoroacetic acid. Suitable bases include, but are not limited to, sodium hydroxide, ammonia, potassium hydroxide and lithium hydroxide.

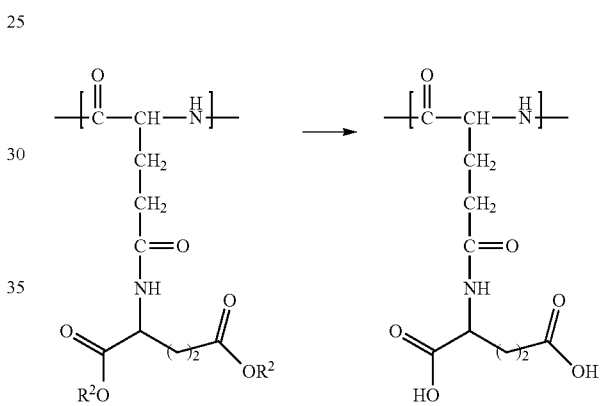

A polymer conjugate (for example, a polymer conjugate that includes recurring units of Formula (IV) and recurring units of Formula (V)) can be formed by reacting an anticancer drug with a portion of the recurring units of Formula (III). As provided herein, the anticancer drug can be selected from taxane, camptothecin, and doxorubicin. Examples of taxanes that can be conjugated to a recurring unit of Formula (III) include paclitaxel and docetaxel.

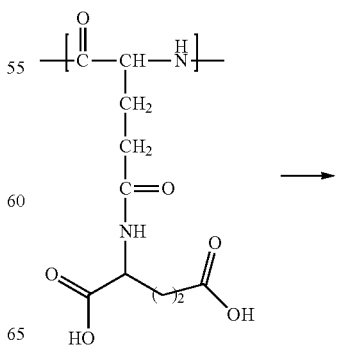

-continued

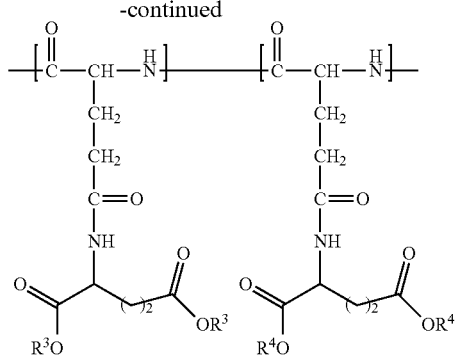

The anticancer drug may be conjugated to the polymer in many different ways. In some embodiments, the anticancer drug can be directly attached to the polymer through an oxygen, a sulfur, a nitrogen and/or carbon atom of the agent. For example, the anticancer drug can be directly attached to a recurring unit of Formula (III) to form a recurring unit of Formula (V). In other embodiments, the anticancer drug can further include a linker group. A linker group is a group that attaches the anticancer drug to the polymer. In some embodiments, the anticancer drug can be attached to a recurring unit of Formula (III) via a linker group to form a recurring unit of Formula (V). The linker group may be relatively small. For instance, the linker group may include an amine, an amide, an ether, an ester, a hydroxyl group, a carbonyl group, or a thiol group. Alternatively, the linker group may be relatively large. For instance, the linker group may include an alkyl group, an alkoxy group, an aryl group, an aryl($C_{1-6}$ alkyl) group, a heteroaryl group, or a heteroaryl ($C_{1-6}$ alkyl) group. In one embodiment, the linker can be —NH(CH$_2$)$_{1-4}$—NH—. In some embodiments, the linker can be —(CH$_2$)$_{1-4}$-aryl-NH—. The linker group can be attached to the anticancer drug at any suitable position. For example, the linker group can be attached in place of a hydrogen at a carbon of the anticancer drug. The linker group can be added to the anticancer drug using methods known to those skilled in the art. In some embodiments, when the anticancer drug is paclitaxel, the paclitaxel can be conjugated via the oxygen atom attached to the C2'-carbon of the paclitaxel. In some embodiments, when the anticancer drug is paclitaxel, the paclitaxel can be conjugated via the oxygen atom attached to the C7-carbon of the paclitaxel.

The anticancer drug can be conjugated to a recurring unit of Formula (III) using various methods. In some embodiments, a polymer that includes recurring units of Formula (III) can be at least partially dissolved in a solvent. Examples of suitable solvents include, but are not limited to, N,N-dimethylformamide (DMF), dimethyl sulfoxide (DMSO), N-methyl-2-pyridone (NMP), and N,N-dimethylacetamide (DMAc). In some embodiments, the solvent can be DMF. The solution of the polymer that includes recurring units of Formula (III) can be combined with the anticancer drug. In some embodiments, a coupling agent can also be combined with the solution of the polymer that includes recurring units of Formula (III) and the anticancer drug. A non-limiting list of coupling agents include the following: 1-ethyl-3-(3-dimethylaminopropyl)-carbodiimide (EDC), 1,3-dicyclohexyl carbodiimide (DCC), 1,1'-carbonyl-diimidazole (CDI), N,N'-disuccinimidyl carbonate (DSC), N-[(dimethylamino)-1H-1,2,3-triazolo-[4,5-b]pyridine-1-yl-methylene]-N-methylmethanaminium hexafluorophosphate N-oxide (HATU), 2-[(1H-benzotriazol-1-yl)-1,1,3,3-tetramethylaminium hexafluorophosphate (HBTU), 2-[(6-chloro-1H-benzotriazol-1-yl)-1,1,3,3-tetramethylaminium hexafluorophosphate (HCTU), benzotriazole-1-yl-oxy-tris-pyrrolidino-phosphonium hexafluorophosphate (PyBOP®), bromo-tris-pyrrolidino-phosphonium hexafluorophosphate (PyBroP®), 2-[(1H-benzotriazol-1-yl)-1,1,3,3-tetramethylaminium tetrafluoroborate (TBTU), and benzotriazol-1-yl-oxy-tris-(dimethylamino)phosphonium hexafluorophosphate (BOP). In some embodiments, the coupling agent can be EDC. In some embodiments, a catalyst can also be combined with the solution of the polymer that includes recurring units of Formula (III) and the anticancer drug. One example of a suitable catalyst is 4-dimethylaminopyridine (DMAP).

The polymer conjugate (for example, a polymer conjugate that includes recurring units of Formula (IV) and recurring units of Formula (V)) can be obtained in the acid form or in the alkali metal salt form. Examples of the acid form and alkali metal salt form of a polymer that includes recurring units of Formula (IV) and recurring units of Formula (V) are shown herein.

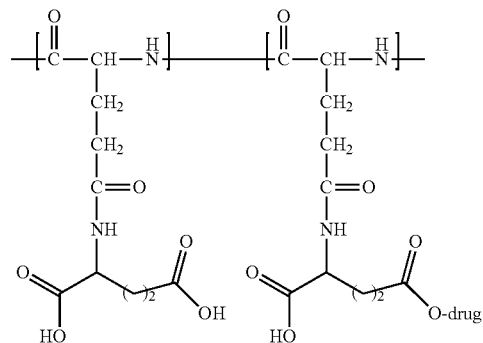

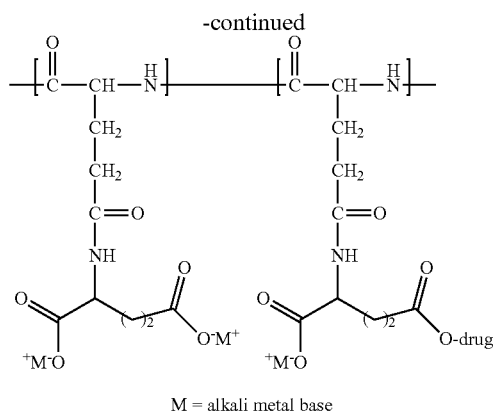

M = alkali metal base

The acid form can obtained using an acid. For example, the solution of the polymer of recurring units of Formula (III) and the anticancer drug can be combined with an acid. Suitable acids include, but are not limited to, hydrochloric acid, hydrobromic acid, nitric acid, nitrous acid, sulfuric acid, sulfonic acid, acetic acid, formic acid, trichloroacetic acid, dichloroacetic acid, chloroacetic acid, glyoxylic acid, oxalic acid, glycolic acid, phosphoric acid, phosphorous acid, malonic acid and trifluoroacetic acid. In some embodiments, the acid can be HCl. The acid form of the polymer conjugate can be transformed to the alkali metal salt form by reacting the acid form with a suitable alkali metal base, such as those described herein. In some embodiments, the base can be sodium bicarbonate. The polymer conjugate can be isolated using a variety of methods. For example, the polymer conjugate can be isolated by centrifugation or filtration.

The polymer conjugate can be purified by various methods. In some embodiments, the polymer conjugate (for example, PGGA-PTX) can be purified by dissolving the polymer conjugate in a suitable solvent and then adding the resulting mixture into a solution. In some embodiments, the suitable solvent can be DMF. In some embodiments, the solution can be an acid solution, such as a HCl solution. The polymer conjugate can be isolated using one or more methods described herein, and then washed with one or more solvent systems. In some embodiments, the one or more solvent systems can be a solution of HCl (for example, 0.2N HCl) and water (such as MilliQ water).

In any of the embodiments described herein, the polymer and/or polymer conjugate can be dried using methods known to those skilled in the art. For example, the polymer and/or polymer conjugate can be air-dried, vacuum dried and/or lyophilized.

EXAMPLES

Example 1

Synthesis of (5-Benzyl Ester Glutamic Acid-N-Carboxyanhydride) (NCA-Ester)

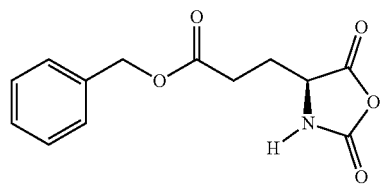 [SMILES: O=C(CC[C@@H]1NC(=O)OC1=O)OCc1ccccc1]

To a 100 L Rot-evaporate system, γ-benzyl-L-glutamate (3.0 kg) and anhydrous THF (30 L) were added. The mixture was stirred for 10 minutes under a nitrogen atmosphere. Triphosgene (1.5 kg) was added in one portion, and the mixture was stirred for 4 hours at 50° C. under a nitrogen atmosphere. The stirring was then stopped and the mixture was cooled to room temperature. N-hexane (50 L) was added with stirring. After addition was complete, the mixture stirred for 30 minutes, and the resulting suspension was stored at −20° C. for 24 hours. The product was isolated as a white precipitate by filtration. The product was then washed with n-hexane to remove excess triphosgene. The product was recrystallized from acetate and n-hexane to provide the NCA-ester (2.6 kg, yield 78%). $^1$H NMR (400 MHz, CDCl$_3$) δ: 2.11 (m, 1H), 2.13 (m, 1H), 2.58 (m, 2H), 4.36 (m, 1H), 5.12 (s, 2H), 6.61 (s, 1H), 7.35 (m, 5H).

Example 2

Synthesis of Poly-L-Glutamate Benzyl Ester (PGA-Bn Ester)

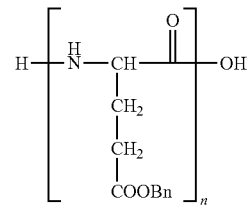

To a solution of anhydrous dioxane (37 L) in a 100 L reactor was added NCA-ester (3.0 kg). The mixture was stirred until the solid dissolved. A solution of NaOMe (12.32 g) in anhydrous MeOH (232.5 mL) with dioxane (2325 mL) was added at room temperature in one portion with vigorously stirring. After an hour, the mixture stood for 72 hours at room temperature resulting in a thick, clear, colorless, viscous solution. This solution was poured slowly into EtOH (400 L) with stirring. The fibrous polymer was isolated by filtration, and washed with EtOH (3×10 L). The polymer was then torn into small pieces and air-dried at room temperature overnight. The polymer was further dried under high vacuum overnight to provide the product as a white fibrous solid (2.22 kg, 89%). $^1$H NMR (400 MHz, d-TFA) δ: 6.67 (m, 5H), 4.57-4.48 (m, 2H), 4.12 (m, 1H), 1.90 (m, 2H), 1.59 (m, 1H), 1.40 (m, 1H).

Example 3

Synthesis of Poly-L-Glutamate Benzyl Ester (PGA-Na Salt)

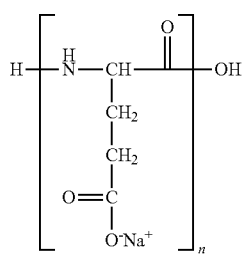

To dichloroacetic acid (40 L) in a dried 100 L reactor equipped with a Teflon coated stir bar was added PGA-Bn ester (1.0 kg). The solution was kept at 28.0° C. overnight under nitrogen atmosphere. A clear viscous solution was formed. A HBr solution (33% in HOAc) (3.5 L) was then added in one portion. The mixture was stirred for a predetermined time, in this case, about 4 hours. The heat was removed and hexane (pre-cooled to −20° C.) (40 L) was added in one portion. PGA precipitated as a white solid. Stirring was stopped after 30 minutes, and the mixture was allowed to settle for 30 minutes at room temperature. The supernatant was removed by vacuum using a cannula. The sediment was suspended and stirred with acetone (40 L) for 30 minutes. The fibrous polymer was isolated by filtration, and the product was washed with acetone (3×10 L) and air-dried for 1 hour.

The resulting residue was transferred to a 50 L flask containing 1N NaHCO$_3$ (aq) (12 L). The mixture was stirred overnight until the solid dissolved. The solution was filtered to provide a clear solution, which was then purified by a tangential flow filtration (TFF) system. The product was lyophilized to provide PGA-Na salt (1.04 kg, 93%). $^1$H NMR (400 MHz, D$_2$O) δ: 4.25-4.20 (m, 1H), 2.27-2.09 (m, 2H), 2.00-1.79 (m, 2H).

Example 4

Synthesis of Poly-(γ-L-Glutamyl-Glutamate) t-Butyl Ester (PGGA-Ester)

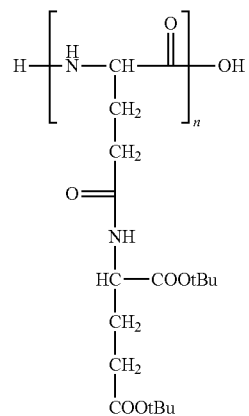

To a solution of anhydrous DMF (25 L) in a 100 L of reactor was added PGA-Na salt (500 g). The mixture was stirred at room temperature for 1 hour. L-glutamic acid di-t-butyl ester hydrochloride (H-Glu(OtBu)$_2$·HCl) (1959 g), HOBt (608 g) and EDC (1904 g) were added in sequence with vigorously stirring. The mixture was stirred at room temperature for 36 hours, and then the mixture was slowly poured into 100 L flask containing MilliQ water (40 L). The mixture was stirred for 30 minutes. The product was isolated by filtration and washed with MilliQ water to obtain purified PGG-ester (1.2 kg, 92%) as a white solid. $^1$H NMR (400 MHz, CDCl$_3$) δ: 8.80 (bs, 1H), 8.47 (bs, 1H), 4.46 (bs, 1H), 4.09 (bs, 1H), 2.39-2.24 (m, 4H), 1.93-1.62 (m, 4H), 1.57-1.25 (m, 18H).

Example 5

Synthesis of Poly-(γ-L-Glutamyl-Glutamate) (PGGA-Acid)

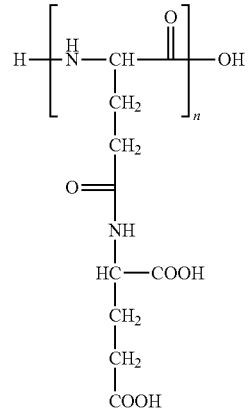

To a 50 L Rot-vapor flask was added PGGA-ester (1100 g) and TFA (8.8 L). The mixture was stirred for 4 hours at room temperature. The TFA was then removed under reduced pressure at 40° C. to form a light yellowish glassy film. The residue was re-dissolved in TFA (4.4), and the mixture was stirred for 16 hours. The TFA was removed under reduced pressure at 40° C., and the residue was dissolved in of MilliQ water (50 L) to provide a light yellow solution. The solution was filtered by suction filtration, and the filtrate was diluted with MilliQ water to 150 L. The solution was then dialyzed by a TFF system. The solution was lyophilized to provide purified PGGA acid (690 g, 94%) as a white solid. $^1$H NMR (400 MHz, D$_2$O) δ: 8.45 (bs, 1H), 4.38 (bs, 1H), 4.14 (bs, 1H), 2.43 (m, 4H), 2.15 (m, 2H), 1.94 (m, 2H).

Example 6

Synthesis of Poly-(γ-L-Glutamyl-Glutamate)-PTX Conjugate (PGGA-PTX)

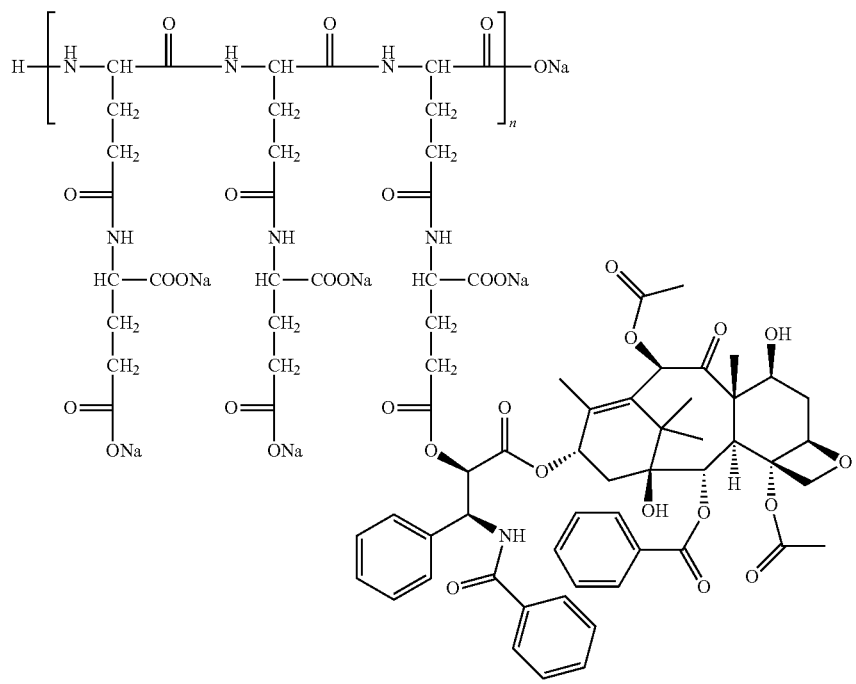

To a solution of anhydrous DMF (50 L) in a 100 L of reactor was added PGGA-acid (1 kg). The mixture was stirred at room temperature for 1 hour, and a clear solution formed. EDC (966 g) and DMAP (142 g) were added in sequence with vigorously stirring. The mixture was stirred for 1 hour under nitrogen atmosphere. A clear solution was formed. PTX (538.5 g) was added in one portion, and the resulting solution was stirred at ambient temperature for 28 hours.

The mixture was then poured slowly into 0.2 N HCl solution (120 L) with stirring. After stirring for 30 minutes, PGGA-PTX in the acid form was isolated by centrifugation. The product was washed with 0.2 N HCl and MilliQ water to provide the crude product as a white solid.

The crude PGGA-PTX in the acid form was dissolved into anhydrous DMF (26 L) with stirring to form a clear solution. The solution was poured slowly into 0.2 N HCl solution (69 L) with stirring. After stirring for 30 minutes, PGGA-PTX in the acid form was isolated by centrifugation. The product was washed with 0.2 N HCl and MilliQ water to provide purified PGGA-PTX in the acid form as a white solid.

The purified PGGA-PTX in the acid form was transferred slowly to 0.3 N NaHCO$_3$(aq) solution (120 L). The mixture was stirred overnight until the solid was dissolved. The pH of the solution was adjusted to a pH in the range of 8.3-8.5 using either sodium bicarbonate or 1H HCl. The solution was filtered to give a clear solution, which was then purified by a TFF system. The product was lyophilized to provide PGGA-PTX (1.5 kg, 97%). $^1$H NMR (400 MHz, D$_2$O) δ: 7.95-7.30 (m, 16H), 5.85-4.85 (m, 4H), 4.45-4.01 (m, 18H), 3.03-2.79 (m, 23H), 2.29-1.51 (m, 85H), 1.05 (m, 6H).

Table 1 is a summary of 3 separate batches of PGGA-PTX obtained from a process described herein at a scale of greater than 300 grams.

TABLE 1

| Polymer Conjugate | Batch | Amount (kg) | Drug Loading (%) | Endotoxin (EU/mg) | MW (kDA) | Poly-dispersity (PDI) |
|---|---|---|---|---|---|---|
| PGGA-PTX | 1 | 1.2 | 38.2 | <0.1 | 76.2 | 1.57 |
| PGGA-PTX | 2 | 0.98 | 36.1 | <0.1 | 78.5 | 1.56 |
| PGGA-PTX | 3 | 1.0 | 37.1 | <0.1 | 77.5 | 1.55 |

As shown in Table 1, the processes described herein provide poly(L-γ-glutamyl-glutamate) anticancer drug conjugates in amounts greater than 300 grams that have consistent weight average molecular weights, low endotoxin content, a narrow range of polydispersity indices and focused drug loading.

Table 2 is a summary of 7 separate batches of PGGA-PTX obtained from a process described herein at a scale of 3-10 grams.

TABLE 2

| Batch | PGGA-PTX (MW) | Polydispersity (PDI) |
| --- | --- | --- |
| 1 | 103.3 | 1.456 |
| 2 | 84.3 | 1.361 |
| 3 | 92.4 | 1.433 |
| 4 | 96.9 | 1.442 |
| 5 | 103.4 | 1.448 |
| 6 | 67.1 | 1.464 |
| 7 | 80.5 | 1.349 |

As shown in Table 2, at a scale below 300 grams, the weight average molecular weights differ by more than 35 kDa. A comparison of Table 1 to Table 2 shows that the processes described herein produce batches of polymer conjugates on a large scale that have consistent weight average molecular weights, low endotoxin content, a narrow range of polydispersity indices and focused drug loading.

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A process of manufacture for preparing batches of a poly(L-γ-glutamyl-glutamate)-anticancer drug conjugate comprising:

polymerizing a compound of Formula (A) to form a polymer having recurring units of Formula (I), wherein $R^1$ is selected from the group consisting of $C_{1-6}$ alkyl, an optionally substituted phenyl and an optionally substituted benzyl;

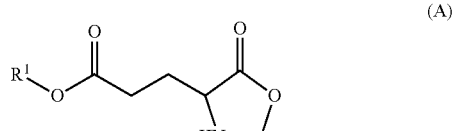

(A)

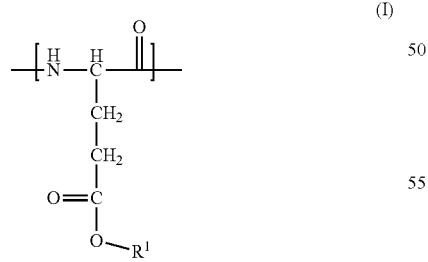

(I)

forming the alkali metal salt of the recurring unit of Formula (I);

reacting the alkali metal salt of the recurring unit of Formula (I) with a compound of Formula (B) to form a polymer having recurring units of Formula (II), wherein each $R^2$ is independently selected from the group consisting of $C_{1-6}$ alkyl, an optionally substituted phenyl and an optionally substituted benzyl;

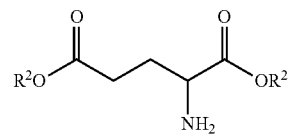

(B)

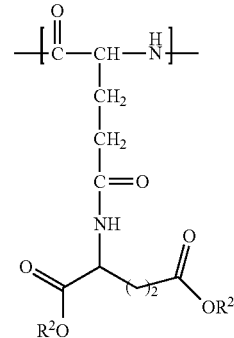

(II)

removing the $R^2$ groups from the recurring units of Formula (II) to form a polymer having recurring units of Formula (III); and

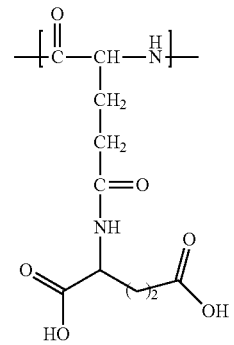

(III)

reacting an anticancer drug with a portion of the recurring units of Formula (III) to form the poly(L-γ-glutamyl-glutamate)-anticancer drug conjugate, wherein the poly (L-γ-glutamyl-glutamate)-anticancer drug conjugate comprises recurring units of Formula (IV) and recurring units of Formula (V):

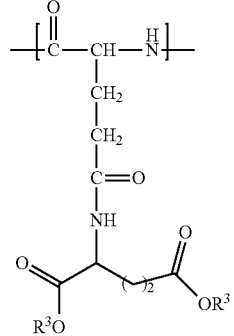

(IV)

-continued

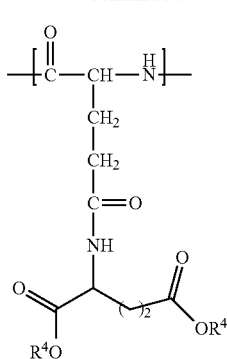

(V)

wherein:
  each $R^3$ is independently hydrogen or an alkali metal; and
  each $R^4$ is independently hydrogen, an alkali metal or the anticancer drug, provided that at least one $R^4$ is the anticancer drug;
  wherein at least 3 batches of poly(L-γ-glutamyl-glutamate)-anticancer drug conjugate are prepared;
  wherein each batch provides an amount of the poly(L-γ-glutamyl-glutamate)-anticancer drug conjugate greater than or equal to about 300 grams; and
  wherein each batch of poly(L-γ-glutamyl-glutamate)-anticancer drug conjugate has one or more characteristics selected from a weight average molecular weight within ±10 kDa from each other batch, a polydispersity in the range of 1.0 to 2.0 and an endotoxin content <0.25 EU/mg.

2. The process of claim 1, wherein each batch has a weight average molecular weight within ±2 kDa from each other batch.

3. The process of claim 1, wherein each batch provides an amount of the poly(L-γ-glutamyl-glutamate)-anticancer drug conjugate greater than about 1.0 kg.

4. The process of claim 1, wherein each batch of the poly(L-γ-glutamyl-glutamate)-anticancer drug conjugate has a polydispersity index in the range of about 1.2 to about 2.0.

5. The process of claim 1, wherein each batch of the poly(L-γ-glutamyl-glutamate)-anticancer drug conjugate has an endotoxin content of less than 0.10 EU/mg.

6. The process of claim 1, wherein each batch of the poly(L-γ-glutamyl-glutamate)-anticancer drug conjugate has a weight average molecular weight in the range of about 60 kDa to about 100 kDa.

7. The process of claim 1, wherein the poly(L-γ-glutamyl-glutamate)-anticancer drug conjugate comprises about 30% to about 40% (weight/weight) of the anticancer drug based on the mass ratio of the anticancer drug to the poly(L-γ-glutamyl-glutamate)-anticancer drug conjugate.

8. The process of claim 1, wherein each $R^1$ is cleaved using an acid solution, and the alkali metal salt is formed using an alkali metal base.

9. The process of claim 8, wherein the alkali metal base is an alkali metal bicarbonate, an alkali metal carbonate or alkali metal hydroxide.

10. The process of claim 9, wherein the alkali metal bicarbonate is sodium bicarbonate.

11. The process of claim 9, wherein the alkali metal hydroxide is sodium hydroxide.

12. The process of claim 8, wherein the acid solution comprises one or more acids.

13. The process of claim 1, wherein the acid solution comprises at least two acids.

14. The process of claim 12, wherein one or more acids are independently selected from hydrochloric acid, hydrobromic acid, nitric acid, nitrous acid, sulfuric acid, sulfonic acid, acetic acid, formic acid, trichloroacetic acid, dichloroacetic acid, chloroacetic acid, glyoxylic acid, oxalic acid, glycolic acid, phosphoric acid, phosphorous, malonic acid and trifluoroacetic acid.

15. The process of claim 1, wherein the acid solution comprises hydrobromic acid and acetic acid.

16. The process of claim 1, wherein the reacting the alkali metal salt of the recurring unit of Formula (I) with a compound of Formula (B) further comprises a coupling agent selected from the group consisting of 1-ethyl-3-(3-dimethylaminopropyl)-carbodiimide (EDC), 1,3-dicyclohexyl carbodiimide (DCC), 1,1'-carbonyl-diimidazole (CDI), N,N'-disuccinimidyl carbonate (DSC), N-[(dimethylamino)-1H-1,2,3-triazolo-[4,5-b]pyridine-1-yl-methylene]-N-methylmethanaminium hexafluorophosphate N-oxide (HATU), 2-[(1H-benzotriazol-1-yl)-1,1,3,3-tetramethylaminium hexafluorophosphate (HBTU), 2-[(6-chloro-1H-benzotriazol-1-yl)-1,1,3,3-tetramethylaminium hexafluorophosphate (HCTU), benzotriazole-1-yl-oxy-tris-pyrrolidino-phosphonium hexafluorophosphate (PyBOP®), bromo-tris-pyrrolidino-phosphonium hexafluorophosphate (PyBroP®), 2-[(1H-benzotriazol-1-yl)-1,1,3,3-tetramethylaminium tetrafluoroborate (TBTU), and benzotriazol-1-yl-oxy-tris-(dimethylamino)phosphonium hexafluorophosphate (BOP).

17. The process of claim 1, wherein the $R^2$ groups are removed by hydrolysis using an acid or a base.

18. The process of claim 17, wherein the acid is selected from hydrochloric acid, hydrobromic acid, nitric acid, nitrous acid, sulfuric acid, sulfonic acid, acetic acid, formic acid, trichloroacetic acid, dichloroacetic acid, chloroacetic acid, glyoxylic acid, oxalic acid, glycolic acid, phosphoric acid, phosphorous acid, malonic acid and trifluoroacetic acid.

19. The process of claim 18, wherein the acid is trifluoroacetic acid.

20. The process of claim 17, wherein the base is selected from sodium hydroxide, ammonia, potassium hydroxide and lithium hydroxide.

21. The process of claim 1, wherein the anticancer drug is selected from taxane, camptothecin, and doxorubicin.

22. The process of claim 21, wherein the taxane is selected from the group consisting of paclitaxel and docetaxel.

23. The process of claim 22, wherein paclitaxel is conjugated to the recurring unit of Formula (V) at the oxygen atom attached to the C2'-carbon or C7-carbon.

24. The process of claim 1, wherein the reacting an anticancer drug with a portion of the recurring units of Formula (III) further comprises a coupling agent selected from the group consisting of 1-ethyl-3-(3-dimethylaminopropyl)-carbodiimide (EDC), 1,3-dicyclohexyl carbodiimide (DCC), 1,1'-carbonyl-diimidazole (CDI), N,N'-disuccinimidyl carbonate (DSC), N-[(dimethylamino)-1H-1,2,3-triazolo-[4,5-b]pyridine-1-yl-methylene]-N-methylmethanaminium hexafluorophosphate N-oxide (HATU), 2-[(1H-benzotriazol-1-yl)-1,1,3,3-tetramethylaminium hexafluorophosphate (HBTU), 2-[(6-chloro-1H-benzotriazol-1-yl)-1,1,3,3-tetramethylaminium hexafluorophosphate (HCTU), benzotriazole-1-yl-oxy-tris-pyrrolidino-phosphonium hexafluorophosphate (PyBOP®), bromo-tris-pyrrolidino-phosphonium hexafluorophosphate (PyBroP®), 2-[(1H-benzotriazol-1-yl)-1,1,3,3-tetramethyl-aminium tetrafluoroborate (TBTU), and benzotriazol-1-yl-oxy-tris-(dimethylamino)phosphonium hexafluorophosphate (BOP).

25. The process of claim 1, wherein the reacting an anticancer drug with a portion of the recurring units of Formula (III) further comprises a catalyst.

26. The process of claim 25, wherein the catalyst is 4-dimethylaminopyridine (DMAP).

27. The process of claim 1, wherein $R^1$ is $C_{1-6}$ alkyl.

28. The process of claim 1, wherein $R^1$ is an optionally substituted phenyl.

29. The process of claim 1, wherein $R^1$ is an optionally substituted benzyl.

30. The process of claim 1, wherein $R^2$ is $C_{1-6}$ alkyl.

31. The process of claim 1, wherein $R^2$ is an optionally substituted phenyl.

32. The process of claim 1, wherein $R^2$ is an optionally substituted benzyl.

33. The process of claim 1, wherein each $R^3$ is hydrogen.

34. The process of claim 1, wherein each $R^3$ is an alkali metal.

35. The process of claim 1, wherein one $R^4$ is hydrogen and the other $R^4$ is the anticancer drug.

36. The process of claim 1, wherein one $R^4$ is an alkali metal and the other $R^4$ is the anticancer drug.

37. The process of claim 1, wherein the alkali metal is sodium.

38. The process of claim 1, further comprising reacting a compound of Formula (1) with triphosgene or phosgene to form the compound of Formula (A), wherein the compound of Formula (1) has the structure:

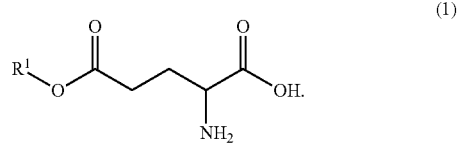

39. The process of claim 1, wherein the poly(L-γ-glutamyl-glutamate)-anticancer drug conjugate comprises about 80 mole % to about 99 mole % of the recurring units of Formula (IV) and the recurring units of Formula (V).

40. The process of claim 1, wherein the poly(L-γ-glutamyl-glutamate)-anticancer drug conjugate consists of, or consists essentially of the recurring units of Formula (IV) and the recurring units of Formula (V).

41. The process of claim 13, wherein the at least two acids are independently selected from hydrochloric acid, hydrobromic acid, nitric acid, nitrous acid, sulfuric acid, sulfonic acid, acetic acid, formic acid, trichloroacetic acid, dichloroacetic acid, chloroacetic acid, glyoxylic acid, oxalic acid, glycolic acid, phosphoric acid, phosphorous acid, malonic acid and trifluoroacetic acid.

* * * * *